United States Patent [19]
Martin et al.

[11] 3,963,696
[45] June 15, 1976

[54] 6,6A-AND 6,7-ANHYDROERYTHROMYCIN B AND DERIVATIVES THEREOF

[75] Inventors: Jerry Roy Martin; John Soloman Tadanier, both of Waukegan; Alma Whitman Goldstein, Lake Bluff, all of Ill.

[73] Assignee: Abbott Laboratories, North Chicago, Ill.

[22] Filed: Feb. 21, 1975

[21] Appl. No.: 551,818

[52] U.S. Cl. .............................. 260/210 E; 424/181
[51] Int. Cl.² ......................................... C07H 17/08
[58] Field of Search ................................ 260/210 E

[56] References Cited
UNITED STATES PATENTS

| | | | |
|---|---|---|---|
| 3,681,326 | 8/1972 | Von Esch | 260/210 E |
| 3,816,397 | 6/1974 | Tadanier et al. | 260/210 E |

*Primary Examiner*—Johnnie R. Brown
*Attorney, Agent, or Firm*—Robert L. Niblack

[57] ABSTRACT

The present invention relates to the preparation of 6,6a-and 6,7-anhydroerythromycin B and derivatives thereof, which are useful as antibiotic.

5 Claims, No Drawings

6,6A- AND 6,7-ANHYDROERYTHROMYCIN B AND DERIVATIVES THEREOF

DETAILED DESCRIPTION

The novel compounds of the invention can be represented by the formulae:

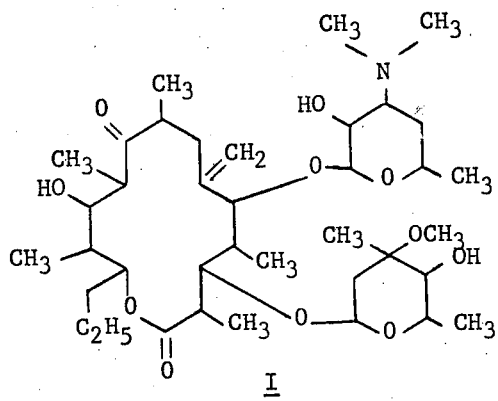

I

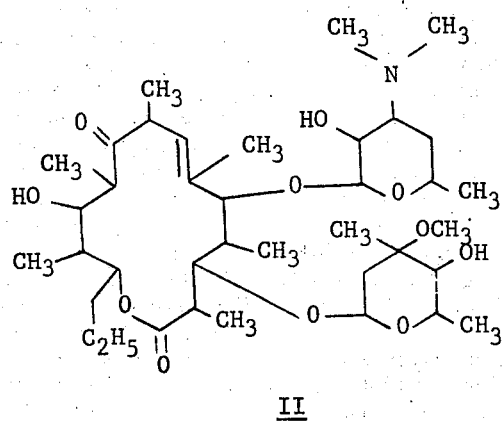

II

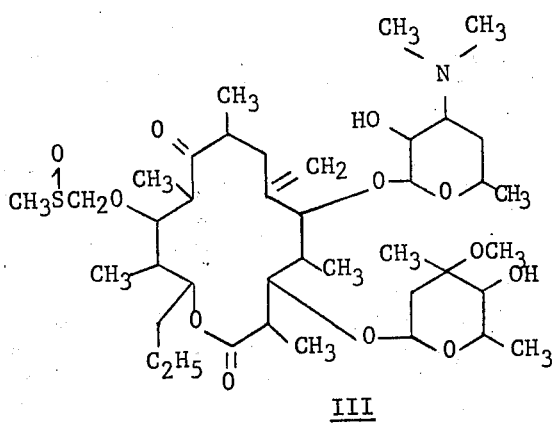

III

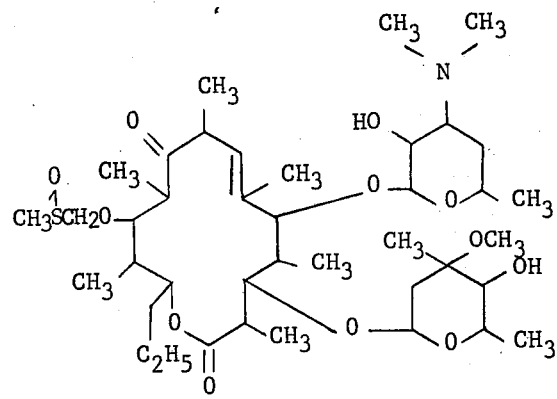

IV

These new compounds exhibit antibiotic activity, and are useful as antibiotic compounds.

According to the present invention, erythromycin B is converted to 4''-O-formylerythromycin B by the method shown in U.S. Pat. No. 3,736,313. The 4''-O-formylerythromycin B is reacted with dimethylsulfoxide and acetic anhydride to produce a crude 11-O-methylthiomethyl-2'-O-acetyl-4''-O-formylerythromycin B.

The 11-O-methylthiomethyl-2'-O-acetyl-4''-O-formylerythromycin B is then reacted with thionylchloride and anhydrous pyridine to give a mixture of 11-O-methylthiomethyl-2'-O-acetyl-4''-O-formyl-6,7-anhydroerythromycin B and 11-O-methylthiomethyl-2'-O-acetyl-4''-O-formyl-6,6a-anhydroerythromycin B. Continued reaction of the product mixture with methanol and 5% sodium bicarbonate gave a crude mixture of 11-O-methylthiomethyl-6,7-anhydroerythromycin B and 11-O-methylthiomethyl-6,6a-anhydroerythromycin B.

Reaction of the mixture of 11-O-methylthiomethyl-6,7-anhydroerythromycin B and 11-O-methylthiomethyl-6,6a-anhydroerythromycin B with Chloramine T, methanol and water gave a mixture of 11-O-methylsulfinyl-methyl-6,6a-anhydroerythromycin B, 11-O-methylsulfinyl-methyl-6,7-anhydroerythromycin B, 11-O-[S-methyl-(p-toluenesulfonylsulfinilimino)methyl]-6,6a-anhydroerythromycin B and 11-O-[S-methyl(p-toluenesulfonylsulfinilimino)methyl]-6,7-anhydroerythromycin B. Continued reaction of this mixture with methanol and hydrochloric acid, followed by chromatography of the mixture, gave 6,7-anhydroerythromycin B (II), 6,6a-anhydroerythromycin B (I), 11-O-methylsulfinylmethyl-6,6a-anhydroerythromycin B (III) and 11-O-methylsulfinylmethyl-6,7-anhydroerythromycin B (IV).

The compounds obtained were then tested against a variety of gram-negative and gram-positive bacteria. Figures are MIC (minimum inhibitory concentration) values in terms of mcg/ml, with erythromycin B used as a standard.

Results are as follows:

| Organism | Erythromycin B | I and II 2 to 1 Ratio | III | IV |
| --- | --- | --- | --- | --- |
| Staphylococcus aureus 9144 | .39 | 12 | 12 | >100 |
| Staphylococcus aureus Smith | .39 | 12 | 12 | 100 |
| Staphylococcus aureus Smith ER | >100 | >100 | >100 | >100 |
| Staphylococcus aureus Wise 155 | >100 | >100 | >100 | >100 |
| Streptococcus faecalis 10541 | 105 | 3.1 | 3.1 | 50 |
| Escherichia coli Juhl | 50 | >100 | >100 | >100 |
| Klebsiella pneumoniae 10031 | 6.2 | >100 | >100 | >100 |
| Proteus Vulgaris Abbott JJ | >100 | >100 | >100 | >100 |
| Proteus micabilis Finland No.9 | >100 | >100 | >100 | >100 |
| Salmonella typhimurium Ed No.9 | 50 | >100 | >100 | >100 |
| Shigella sonnei 9290 | 25 | >100 | >100 | >100 |
| Pseudomonas aeruginosa BMH No.10 | 50 | >100 | >100 | >100 |
| Streptococcus pyogenes Roper | >100 | >100 | >100 | >100 |
| Staphylococcus aureus Quinones | >100 | >100 | >100 | >100 |
| Streptococcus pyogenes Scott | >100 | >100 | >100 | >100 |
| Streptococcus pyogenes RO | | | | |
| Mycobacterium gallisopteum S6 | .02 | 10 | 25 | 50 |
| Mycobacterium granularum 19168 | .01 | 50 | 2.5 | 100 |
| Mycobacterium hyorhinis 17981 | 50 | >100 | >100 | >100 |
| Mycobacterium pneumoniae FH | .01 | 2.5 | .5 | 25 |
| Haemophilus influenzae Patterson | 1.56 | >100 | >100 | >100 |
| Haemophilus influenzae Brimm CSF | 1.56 | >100 | >100 | >100 |
| Haemophilus influenzae Shemwell | 1.56 | >100 | >100 | >100 |
| Haemophilus influenzae Illinois | 1.56 | >100 | >100 | >100 |
| Haemophilus influenzae Terry | 1.56 | >100 | >100 | >100 |
| Crithidia fascicalata | >100 | >100 | >100 | >100 |
| Trichomonas vaginalis CLMI | >100 | >100 | >100 | >100 |
| Haemophilus influenzae 9334 | 3.1 | >100 | >100 | >100 |

Reference to the following specific examples will serve to illustrate the foregoing reaction scheme used in the preparation of the compounds of the invention.

EXAMPLE I

11-O-Methylthiomethyl-2'-O-acetyl-4''-O-Formylerythromycin B

A solution prepared from 15.0 g. of 4''-O-formylerythromycin B, 150 ml. of dimethylsulfoxide, and 105 ml. of acetic anhydride was allowed to stand at room temperature for 20 hours. The reaction mixture was slowly added to a mixture prepared from 600 ml. of ice-water and 110 g. of sodium carbonate. Additional ice was added as necessary to keep the mixture cold for a total final volume of approximately 1200 ml. The neutralized reaction mixture was extracted three times with 500 ml. portions of chloroform. The combined chloroform extracts were washed once with 1000 ml. of 5% sodium bicarbonate, three times with 1 liter portions of water and dired over anhydrous magnesium sulfate. The chloroform was evaporated under reduced pressure and the residual dimethylsulfoxide removed by azeotropic distillation with benzene under reduced pressure to leave 17.4 g. of crude 11-O-methylthiomethyl-2'-O- acetyl-4''-O-formylerythromycin B as a light yellow-brown foam, IR: 3603, 3500 (broad), 1727 and 1704 (sh) cm$^{-1}$: NMR: $\delta$ 2.04 (CO$_2$CH$_3$), 2.25 (SCH$_3$), 2.28 [N(CH$_3$)$_2$], 3.37 (OCH$_3$), 8.19 (CHO).

EXAMPLE II

11-O-Methylthiomethyl-2'-O-Acetyl-4''-O-Formyl-6,7-Anhydroerythromycin B, 11-O-Methylthiomethyl-2'-O-Acetyl-4''-O-Formyl-6,6a-Anhydroerythromycin B A stirred solution prepared from 8.7 g. of 11-O-methylthiomethyl-2'-O-acetyl-4''-O-formylerythromycin B (prepared as in Example I), 86.5 ml. of anhydrous pyridine and cooled in an ice-water bath was treated dropwise with a solution prepared from 8.65 ml. of thionylchloride and 86.5 ml. of anhydrous pyridine. Stirring was continued for one hour at ice-water temperatures. The reaction mixture was poured into 2000 ml. of ice-water containing excess sodium bicarbonate. The solution was extracted twice with 1000 ml. portions of ether and dried over anhydrous magnesium sulfate. Evaporation of the ether under reduced pressure and removal of the residual pyridine by azeotropic distillation under reduced pressure with benzene gave 8.0 g. of a crude mixture of 11-O-methylthiomethyl-2'-O-acetyl-4''-O-formyl-6,7-anhydroerythromycin B and 11-O-methylthiomethyl-2'-O-acetyl-4''-O- formyl-6,6a-anhydroerythromycin B as a light tan foam, IR: 1726 and 1700 (sh) cm$^{-1}$; NMR: $\delta$ 1.77 (vinylmethyl), 2.05, 2.12 (CO$_2$CH$_3$), 2.14, 2.18 (SCH$_3$), 2.25, 2.27 [N(CH$_3$)$_2$], 3.27, 3.37 (OCH$_3$), 5.00, 5.36 (vinyl proton).

EXAMPLE III

11-O-Methylthiomethyl-6,7-Anhydroerythromycin B, 11-O-Methylthiomethyl-6,6a-Anhydroerythromycin B A solution prepared from 7.99 g. of product mixture from Example II, 170 ml. of methanol, and 17 ml. of 5% sodium bicarbonate solution was stirred for 72 hours at room temperature. The major portion of the methanol was evaporated under reduced pressure and the residue shaken with a mixture of 700 ml., 5% sodium bicarbonate solution and 700 ml. chloroform. The aqueous phase was extracted with a second 700 ml. portion of chloroform. The combined chloroform extracts were washed three times with 700 ml. portions of water and dried over anhydrous magnesium sulfate. Evaporation of the chloroform under reduced pressure gave 7.4 g. of a crude mixture of 11-O-methylthiomethyl-6,7-anhydroerythromycin B and 11-O-methylthiomethyl-6,6a-anhydroerythromycin B as a light-colored foam, IR: 3540, 3300–3500 (broad), 1726, 1715 (sh) and 1701 (sh) cm$^{-1}$; NMR: δ 1.81 (vinylmethyl), 2.11, 2.18 (SCH$_3$), 2.28, 2.32 [N(CH$_3$)$_2$], 3.25, 3.31 (OCH$_3$), 4.99, 5.38 (vinyl proton).

EXAMPLE IV

11-O-Methylsulfinylmethyl-6,6a-Anhydroerythromycin B,
11-O-Methylsulfinylmethyl-6,7-Anhydroerythromycin B A solution prepared from 750 mg. of product mixture prepared in Example 3, 8.5 ml. methanol and 1.5 ml. water was treated with a solution prepared from 625 mg. of Chloramine T, 8.5 ml. methanol, and 1.5 ml. water. The reaction mixture was allowed to stand at room temperature for 75 minutes then it was shaken with 75 ml. of cold 5% sodium bicarbonate and 100 ml. of chloroform. The aqueous phase was separated and extracted with 100 ml. of chloroform. The combined chloroform extracts were washed three times with water and dried over anhydrous magnesium sulfate. Evaporation of the chloroform under reduced pressure left a white foam containing a mixture of 11-O-methylsulfinylmethyl-6,6a-anhydroerythromycin B, 11-O-methylsulfinylmethyl-6,7-anhydroerythromycin B, 11-O-[S-methyl-(p-toluenesulfonylsulfinilimino)methyl]-6,6a-anhydroerythromycin B and 11-O-[S-methyl(p-toluenesulfonylsulfinilimino)methyl]-6,7-anhydroerythromycin B; IR: 3545, 3500–3300 (broad complex), 1724, 1703 (sh), 1599 (w) and 1490 (w) cm$^{-1}$; NMR: δ 1.83 (vinylmethyl), 2.29 [N(CH$_3$)$_2$], 3.32, 3.31 (OCH$_3$), 7.25, 7.80 (ARH).

EXAMPLE V 6,7-Anhydroerythromycin B,
6,6a-Anhydroerythromycin B

A stirred solution prepared from 8.0 g. of product prepared as in Example 4 and 120 ml. methanol was treated with 40 ml. of 0.4 N. hydrochloric acid. The solution was stirred at room temperature for 30 minutes then poured into 500 ml. of 5% sodium bicarbonate. The product was extracted with two 300 ml. portions of chloroform. The chloroform extract was washed three times with 300 ml. volumes of water and dried over anhydrous magnesium sulfate. Evaporation of the chloroform left 7.7 g. of white foam. 4.0 g. of the product thus obtained was chromatographed on a column of silica gel (5.8 × 75 cm) according to published procedures [Olienick and Corcoran, *Journal of Biological Chemistry*, Vol. 244, No. 727 (1969)]. Elution gave fractions containing a mixture of 6,7-anhydroerythromycin B (II) and 6,6a-anhydroerythromycin B (I). These fractions were pooled and concentrated to dryness under reduced pressure. The residue was dissolved in chloroform and washed three times with water to remove residual inorganic salts. Drying over anhydrous magnesium sulfate and concentration under reduced pressure left 274 mg. of white foam containing a mixture of 6,7-anhydroerythromycin B (II) and 6,6a-anhydroerythromycin B (I) in an approximate 1:2 ratio: IR: 3540, 3300–3500 (broad complex), 1725 (sh), and 1700 cm$^{-1}$; NMR: δ 1.85 (vinylmethyl), 2.29 [N(CH$_3$)$_2$], 3.25, 3.29 (OCH$_3$), 5.32, 5.03 (vinyl proton).

EXAMPLE VI

11-O-Methylsulfinylmethyl-6,6a-Anhydroerythromycin B,
11-O-Methylsulfinylmethyl-6,7-Anhydroerythromycin B Continued elution gave fractions containing pure 11-O-methylsulfinylmethyl-6,6a-anhydroerythromycin B (III). Work up as described above gave 361 mg. of colorless foam, [α]$_D^{23}$ − 93.2°; IR: 3504, 3300–3500 (broad), 1726 and 1703 cm$^{-1}$; NMR: δ 5.34, 4.97 (vinyl proton), 2.30 [N(CH$_3$)$_2$], 2.54, 2.55

3.26 (OCH$_3$).

Continued elution gave fractions containing a mixture of 11-O-methylsulfinylmethyl-6,6a-anhydroerythromycin B (III) and 11-O-methylsulfinylmethyl-6,7-anhydroerythromycin B (IV). Finally fractions containing pure 11-O-methylsulfinylmethyl-6,7-anhydroerythromycin B (IV) were eluted and collected. Work up as above gave 225 mg. of colorless foam, [α]$_D^{23}$ − 109.6°; IR: 3545. 3300–3500 (broad), 1728 and 1704, cm$^{-1}$. NMR: δ 1.83 (vinylmethyl), 2.30 [N(CH$_3$)$_2$], 2.48

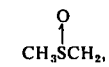

3.31 (OCH$_3$).

What is claimed is:

1. A compound having the formula

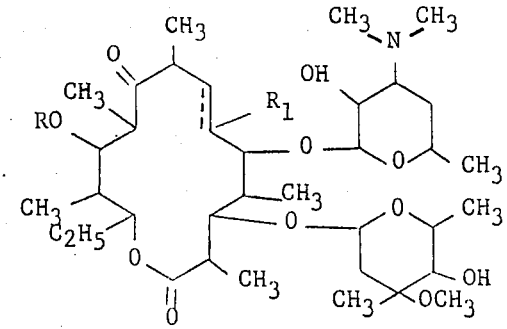

wherein R is hydrogen or $$\overset{O}{\underset{\|}{CH_3SCH_2,}}$$

R$_1$ is =CH$_2$ or —CH$_3$, and --- in position 6,7 indicates the presence of a possible double bond.

2. A compound according to claim 1, 6,7-anhydroerythromycin B.

3. A compound according to claim 1, 6,6a-anhydroerythromycin B.

4. A compound according to claim 1, 11-O-methylsulfinyl-6,6a-anhydroerythromycin B.

5. A compound according to claim 1, 11-O-methylsulfinylmethyl-6,7-anhydroerythromycin B.

* * * * *